United States Patent [19]

Markonius

[11] Patent Number: 5,591,771
[45] Date of Patent: Jan. 7, 1997

[54] USE OF PROPOLIS COMPONENTS AS AN ADJUVANT

[75] Inventor: Maria Markonius, Johanneshor, Sweden

[73] Assignees: Michel Fockerman, Ljungbyhed; Jasmine Fockerman Cederqvist, Stockholm, both of Sweden

[21] Appl. No.: 474,103

[22] Filed: Jun. 7, 1995

Related U.S. Application Data

[63] Continuation-in-part of Ser. No. 809,420, Dec. 17, 1991, Pat. No. 5,449,794.

[51] Int. Cl.$^6$ .................................................. A61K 31/35
[52] U.S. Cl. ............................................................ 514/456
[58] Field of Search ............................................. 514/456

[56] References Cited

U.S. PATENT DOCUMENTS

| | | | |
|---|---|---|---|
| 4,297,348 | 10/1981 | Frazier | 424/180 |
| 4,352,792 | 10/1982 | Ishitsuka et al. | 424/180 |
| 4,866,080 | 9/1989 | Timar et al. | 514/456 |

FOREIGN PATENT DOCUMENTS

| | | | |
|---|---|---|---|
| 1057349 | 2/1967 | Germany . | |
| 2145082 | 3/1985 | United Kingdom | C07D 311/22 |

OTHER PUBLICATIONS

CA 91:84014 (1979).
Metzner et al., Zur antimikrobiellen Wirksamkeit von Propolis und Propolisinhaltsstoffen, Pharmazie 34, H.2 (1979), pp. 97–102.
Dictionary of Organic Compounds, vol. Two, Fifth Edition, Clos–Dop.
Villaneuva, Barbier, Gonnet, Lavie. 1970. Propolis flavonoids. Isolation of a new bacteriostatic substance, pinocembrin (5,7–dihydroxyflavanone). Ann. Inst. Pasteur, Paris 118(1), 85–7.
Metzner, Schneidewind, Friedrich. 1977. Effects of propolis and pinocembrim on blastomyces. Pharmazie 32(11), 730.
Hufford, Lasswell. 1978. Antimicrobial activities of constituents of *Uvaria chamae*. Llyodia 41(2), 156–160.
Metzner, Schneidewind. 1978. Effect of pinocembrin on the course of experimentally–induced Candida infections in the mouse. Mykosen 21(8), 257–62.
Metzner, Bekemeier, Schneidewind, Wenzel. 1979. Pharmacokinetic studies of the propolis constituent pinocembrin in the rat. Pharmazie 34(3), 185–7.
Metzner, Bedemeier, Paintz, Schneidewind. 1979. Antimicrobial activity of propolis and propolis constituents. Pharmazie 34(2), 97–102.
Mitscher, Rao, Khanna, Veysoglu. 1983. Antimicrobial agents from higher plants: prenylated flavonoids and other phenols from *Glycyrrhiza lepidota*. Phytochemistry 22(2), 573–6.
Bogdanov. 1984. Characterization of antibacterial substances in honey. Lebensm.–Wiss. Technol. 17(2) 74–6.
Pepeljnjad, Jalsenjak, Maysinger. 1985. Flavonoid content in propolis extracts and growth inhibition of *Bacillus subtilis*. Pharmazie 40(2), 122–3.
Papay, Soltesz, Csizmadia, Toth. 1987. Chemical and pharmacological study of propolis samples of various locations. Acta Pharm. Hung. 57(3–4), 143–51.

*Primary Examiner*—Amelia Owens
*Attorney, Agent, or Firm*—Lynn E. Barber

[57] ABSTRACT

A method of providing adjuvant activity utilizing one or more of the components of propolis, such as the benzopyran phenol derivates, pinocembrin, pinobanksin-3-acetate and naringenin, and preferably using these three components combined.

9 Claims, 1 Drawing Sheet

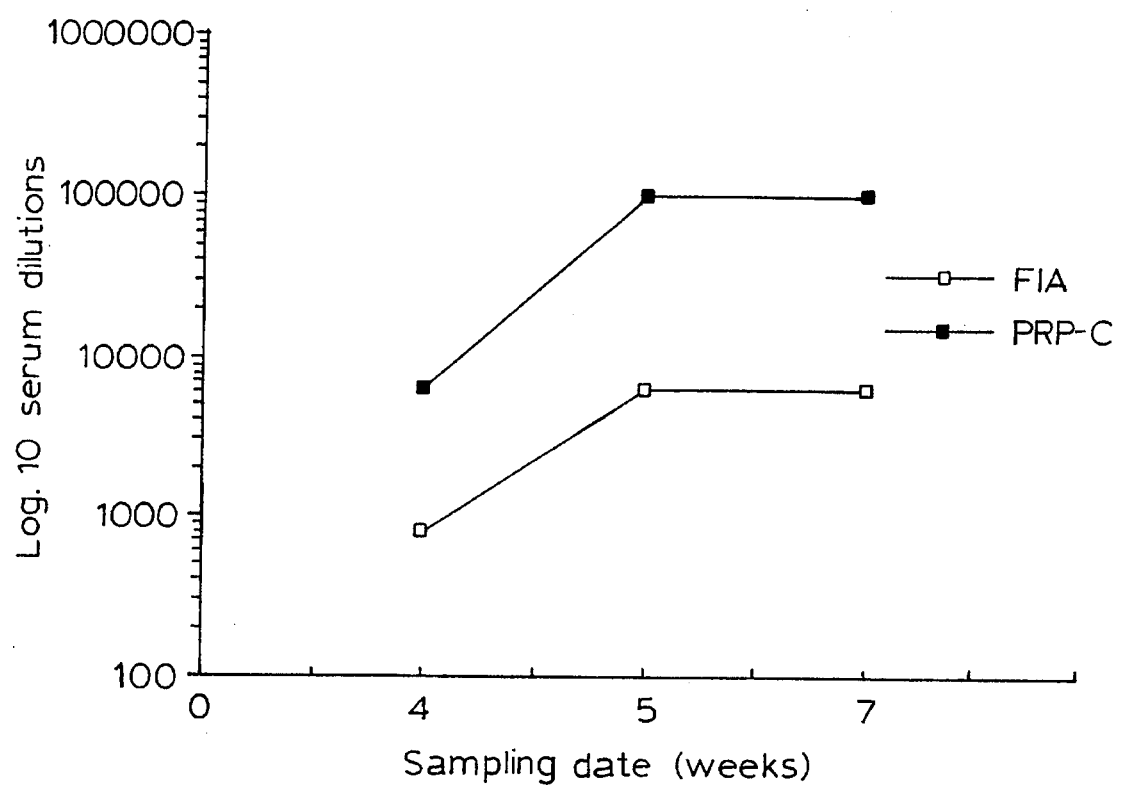

USE OF PROPOLIS COMPONENTS AS AN ADJUVANT

CROSS REFERENCE TO RELATED APPLICATIONS

This is a continuation-in-part of U.S. patent application Ser. No. 07/809,420, filed Dec. 17, 1991, now U.S. Pat. No. 5,449,794.

BACKGROUND OF THE INVENTION

1. Field of the Invention

This invention relates to compositions which have improved adjuvant activity and which are non-toxic.

2. Description of the Related Art

Many substances are not highly antigenic unless associated with other substances, which are termed adjuvants. Adjuvants are generally lipid substances which enhance the effectiveness of antigens in stimulating the production of antibodies. Adjuvants are used to make immnunizing preparations such as vaccines. This enhanced effectiveness may decrease the number of immunizations needed and/or increase overall protection provided by the immunization.

Substances such as the waxy substances in cells of dead cells of Mycobacterium, lanolin, and aqueous emulsions of vegetable oils or mineral oil have thus been used as adjuvants. A well-known type of adjuvant is Freund's adjuvant, which is an aqueous emulsion of mineral oil mixed with heat-killed tubercle bacilli.

As efforts continue to provide more efficient, safe antibody production, researchers have continued to try to find better adjuvants. The demand for more potent and nontoxic adjuvants for human and animal vaccines is thus steadily growing.

It is therefore an object of this invention to provide an adjuvant which has increased efficiency.

It is a further object of this invention to provide an adjuvant having low or no toxicity.

Other objects and advantages will be more fully apparent from the following disclosure and appended claims.

SUMMARY OF THE INVENTION

Compounds of the general formula

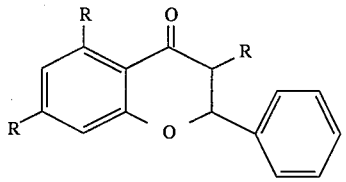

which have been extracted from propolis and are benzopyran phenol derivates, have been found to have adjuvant activity. In particular, a composition containing pinocembrin, pinobanksin, or naringenin, or preferably, a combination of these three compounds, has adjuvant activity significantly greater than Freund's incomplete adjuvant.

Other aspects and features of the invention will be more fully apparent from the following disclosure and appended claims.

BRIEF DESCRIPTION OF THE DRAWINGS

FIG. 1 is a graph of the results of Example 3 showing the adjuvant effect of PRP-C-AD (Propino-Compound-Adjuvant) containing the three benzopyran derivates compared with Freund's Incomplete Adjuvant using 5 µg envelope proteins of EHV-2 as the antigen.

DETAILED DESCRIPTION OF THE INVENTION AND PREFERRED EMBODIMENTS THEREOF

The present invention is a method of providing increased adjuvant effectiveness, comprising utilizing as an adjuvant, a compound of the general formula:

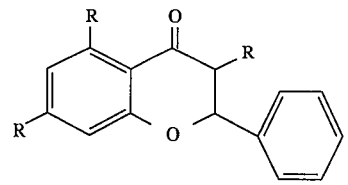

Preferably the compound comprises pinocembrin, pinobanksin-3-acetate or naringenin, and most preferably a combination of these three compounds is used as the adjuvant.

The compounds are preferably derived from propolis by methods disclosed in co-pending U.S. application Ser. No. 07/809,420, the disclosure of which is incorporated herein. In particular, the derivation according to Example 10 of this application is the preferred method, and is as follows: as in Example 1, in the extraction vessel, 500 liters of an ethanolic solution not less than 87% by weight in water is prepared. While the mixture is being stirred, 20 kg of the ground propolis is added to the contents of the extractor. The batch is subjected to ultrasonic extraction (18–25 kHz) for 25 minutes, then left for two hours, decanted and filtered. The filtration is effected via a pressure filter with rapid filter-paper inserts. The clear propolis extract is reduced to a concentration of 20 weight %. Thereafter, the procedure of Example 2 is repeated (the extract obtained in Example 1 is diluted to contain a dry substance weight of 10% in alcohol. NaCl is dissolved in distilled water to a concentration of 0.9%. 700 ml of the solution is placed in a beaker which is put into a water bath. The temperature in the beaker is kept at 30° C. 300 ml of the propolis extract containing 10 weight % propolis in ethanol is added drop by drop to the NaCl over about a 5 hour period). After adding the propolis extract drop by drop to the NaCl solution, the mixture is heated at 60° for 72 to 78 hours. Analysis of the yellow solution with mass spectra shows that it contains pinocembrin, pinobanksin-3-acetate and naringenin.

The compounds used as an adjuvant according to the present invention are used in the same manner as adjuvants known in the art but do not require the laborious preparative techniques for effective use. For example, most adjuvants like Freund's Complete (FCA) or incomplete (FIA) adjuvants or aluminum hydroxide require extensive procedures when formulated into a vaccine. The substance is formed into a gel or emulsion, to which the vaccine antigen is absorbed in order to form gel stringent conditions. PRP-C needs only to be added to the vaccine antigen without requiring prior formation of an emulsion or gel and antigen absorption. PRP-C is thus easily utilized for both human and animal requirements.

The features and advantages of the present invention will be more clearly understood by reference to the following examples, which are not to be construed as limiting the invention.

EXAMPLES

Example 1

As described in Example 10 of co-pending application Ser. No. 07/809,420, to obtain the PRP-C-AD extract used for these experiments, 500 liters of an ethanolic solution not less than 87% by weight in water is prepared. While the mixture is being stirred, 20 kg of the ground propolis is added to the contents of the extractor. The batch is subjected to ultrasonic extraction (18–25 kHz) for 25 minutes, then left for two hours, decanted and filtered.

The filtration is effected via a pressure filter with rapid filter-paper inserts. The clear propolis extract obtained is reduced to a concentration of 20% of the dry substance in a column concentrator in a 150—50 mm $H_2O$ vacuum by means of a heat pump. The concentration is performed at a temperature of no greater than 20° C.

NaCl is dissolved in distilled water to a concentration of 0.9%. 500 ml of the solution is placed in a beaker which is put into a water bath. The temperature in the beaker is kept at 30° C. 500 ml of the propolis extract containing 20 weight % propolis in ethanol is added drop by drop to the NaCl over about a 5 hour period. The mixture is heated at 60° C. for 72–78 hours. A muddy brown precipitate is obtained. The temperature of the solution is controlled by keeping the water bath boiling and by continuously adding water for 15 hours to keep the water level. By then a light yellow solution is formed in a volume of about 700 ml, with the rest of the solution evaporated during the heating. The beaker containing the solution is left in the water bath until the contents have reached room temperature. The precipitate is separated from the solution.

The light yellow solution is further purified by dialysis against water. 50 ml of the extract is dialyzed against 250 ml of distilled water through a dialysis tube (Model mw tatar 3500, Kebo AB, Sweden). The purified product contains purified pinobanksin-3-acetate, pinocembrin and naringenin, all interacting together in a NaCl solution.

Example 2

To determine toxicity, purified PRP-C-AD in NaCl was tested in mice at a dose of 1 µg per mouse. The animals were divided into two groups, each consisting of six 12-week old female BALB/c mice. The preparation was given to the animals either subcutaneously or intraperitoneally. No lethal effect was noticed during the observation period of three weeks. Minor local reactions consisting of a depletion of hair at the injection site, were observed in two of the six animals inoculated subcutaneously.

Example 3

To determine effectiveness of PRP-C-AD as an adjuvant, two groups of 12 week old female BALB/c mice were used with six animals per group. The antigen used for immunization was the envelope glycoproteins of Equine herpesvirus type-2 (EHV-2). The dose of antigen was 5 µg protein for each of the two different preparations as measured by the Bradford method, where bovine serum albumin (BSA) was used as a standard. An aliquot 50 µl of the PRP-C-AD sample was mixed with 2.5 ml of the protein-dye binding reagent, and the change in color intensity was measured with a spectrophotometer at 595 nm (Bradford, M. A., Rapid and Sensitive Method for the Quantification of Microgram Quantities of Protein Utilizing the Principle of Protein-Dye Binding. Anal. Biochem. 72:2248–254, 1976).

The mice in Group A received the antigen mixed with Freund's incomplete adjuvant (FIA). To do this, antigen at 5 µg protein, as measured by the Bradford method was mixed with FIA. The amount of FIA is a default standard quantity.

Group B mice received the antigen mixed with 1 µg PRP-C using the same technique as with the FIA.

The mice were immunized twice, four weeks apart. Blood samples were taken at weeks 4, 5 and 7 after the first immunization. The serum was separated and inactivated for 1 hour at 56° C. Serum antibody response to the envelope antigen was measured using the ELISA technique to determine the virus antibody liters in the sera of the mice (Voller, A., Bartlett, A., Bidwell, D. E. The Use of Enzymelinked Immunosorbent Assay in Serology of Viral and Parasitic Diseases, Scand. J. Immunol. 8:123–129, 1978). Briefly, ELISA plates (Nunk, Copenhagen, Denmark) were coated with purified virus antigen at a concentration of 2 µg per well. Sera to be tested were diluted in phosphate-buffered saline (PBS) containing 0.2% TWEEN 20™. Bound mouse IgG were detected by the addition of rabbit anti-mouse IgG conjugated to horseradish peroxidase (Dakopatts, Roskilde, Denmark). The substrate used was 5 mM 1,2 phenyldiamine (Merck, Damstadt, Germany) and 3.5 mM $H_2O_2$ in substrate buffer (34 mM citric acid, 66 mM disodium hydrogen orthophosphate). The enzyme reaction was stopped after 30 minutes with 2M $H_2SO_4$ and the absorbance was read at 492 nm with a Titerteck Multiscan spectrophotometer (Flow Laboratories, Irvine, United Kingdom). The serum antibody response of the mice (mean values of highest dilutions that give antibody response) are shown in Table I.

TABLE I

| Animal Group | Weeks post immunization | | |
| --- | --- | --- | --- |
| | 4 | 5 | 7 |
| A | 1/800 | 1/6400 | 1/6400 |
| B | 1/6400 | 1/102400 | 1/102400 |

The difference between the two treatments shown in Table 1 can be seen more clearly in the graph in FIG. 1. These results show that PRP-C is superior to the standard, widely used adjuvant FIA. Animals receiving the antigen and the product of Example 1 in this test show about 16 times higher antibody titers than animals receiving antigen and FIA.

The tests used in the Examples and the methods deployed therein are the standard tests to determine the function of an adjuvant. The results that one achieves is that a combination of the antigen and adjuvant in these experiments create antibodies, which is what happens in the body as well.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of providing an adjuvant effect, comprising utilizing as an adjuvant, a compound selected from the group consisting of pinocembrin, pinobanksin-3-acetate, and naringenin.

2. A method according to claim 1, wherein the compound is pinocembrin.

3. A method according to claim 1, wherein the compound is pinobanksin-3-acetate.

4. A method according to claim 1, wherein the compound is naringenin.

5. A method according to claim 1, wherein a mixture of pinocembrin, pinobanksin-3-acetate, and naringenin is applied.

6. An adjuvant composition, comprising an extract solution containing pinocembrin, pinobanksin-3-acetate and naringenin.

7. The adjuvant composition of claim 6, wherein said solution is a physiological solution of NaCl.

8. The adjuvant composition of claim 7, wherein the composition is contains 0.6–0.9% NaCl.

9. The adjuvant composition of claim 8, wherein the composition contains 0.9% NaCl.

* * * * *